US008486672B2

(12) United States Patent
Yoshida et al.

(10) Patent No.: US 8,486,672 B2
(45) Date of Patent: Jul. 16, 2013

(54) METHOD OF PRODUCING LAURIC ACID OR AN ESTER THEREOF

(75) Inventors: Hiroshi Yoshida, Cincinnati, OH (US); Fumikazu Takahashi, Haga-gun (JP); Yasushi Takimura, Haga-gun (JP)

(73) Assignee: Kao Corporation, Tokyo (JP)

( * ) Notice: Subject to any disclaimer, the term of this patent is extended or adjusted under 35 U.S.C. 154(b) by 72 days.

(21) Appl. No.: 13/070,974

(22) Filed: Mar. 24, 2011

(65) Prior Publication Data

US 2012/0245369 A1    Sep. 27, 2012

(51) Int. Cl.
*C12P 7/64* (2006.01)

(52) U.S. Cl.
USPC .......................................................... 435/134

(58) Field of Classification Search
None
See application file for complete search history.

(56) References Cited

U.S. PATENT DOCUMENTS

2011/0217743 A1    9/2011    Yoshida et al.

FOREIGN PATENT DOCUMENTS

WO    WO 2009/103065 A2    8/2009
WO    WO 2011/108755 A1    9/2011

OTHER PUBLICATIONS

Leblond et al., Phycologia 48 (2): 101-104 (2009).*
Leblond et al., Phycologia 48(2): 101-104 (2009).*
Leblond et al., J. Phycol. 36: 1103-1108 (2000).*
Yabuuchi et al., Animal Science Journal 77:300-307 (2006).*
Gile et al., J. Phycol. 46: 743-750 (2010).*
http://www.egc.com/useful_info_lighting.php, accessed Aug. 13, 2012.*
Chisti, Y, "Biodiesel from microalgae," Biotechnology Advances 25(3): 294-306 (May 2007), Oxford: Elsevier Science, New York.
Gouveia, L et al., "*Neochloris oleabundans* UTEX #1185: a suitable renewable lipid source for biofuel production," J Ind Microbiol Biotechnol 36(6): 821-826 (Jun. 2009), Houndmills, Great Britain.
Henderson, RJ et al, "Lipid composition and biosynthesis in the marine dinoflagellate *Crypthecodinium cohnii*," Phytochem 27(6): 1679-1683 (1988), Pergamon Press, Great Britain.
International Search Report (ISR) for PCT/JP2011/055434, I.A. fd: Mar. 2, 2011, mailed by the European Patent Office, Rijswijk, Netherlands on Aug. 10, 2011.
Written Opinion of the International Searching Authority for PCT/JP2011/055434, I.A. fd: Mar. 2, 2011, mailed by the European Patent Office, Berlin, Germany on Aug. 10, 2011.
Harland, AD et al, "Distribution of lipids between the zooxanthellae and animal compartment in the symbiotic sea anemone *Anemonia viridis*: wax esters, triglycerides and fatty acids," Marine Biology 110: 13-19 (Feb. 1991), Springer, Berlin, Germany.
Treignier, C et al, "Effect of light and feeding on the fatty acid and sterol composition of zooxanthellae and host tissue isolated from the scleractinian coral *Turbinaria reniformis*," Limnology and Oceanography, 53(6): 2702-2710 (Nov. 2008), American Society of Limnology and Oceanography, Inc., Waco, TX.
Parrish, CC et al, "Time courses of intracellular and extracellular lipid classes in batch cultures of the toxic dinoflagellate, *Gymnodinium* cf. *nagasakiense*," Marine Chemistry 48(a): 71-82 (Dec. 1994), Elsevier, Amsterdam, Netherlands.
International Search Report (ISR) and Written Opinion (WO) for PCT/JP2012/058505, I.A. fd: Mar. 23, 2012, ISR mailed by the European Patent Office, Rijswijk, Netherlands on Jun. 12, 2012.
Radakovits, R et al., "Genetic engineering of fatty acid chain length in *Phaeodactylum tricornutum*," Metab Eng 13(1): 89-95 (Jan. 2011), Academic Press, Brugge, Belgium.
Roche, SA and JD Leblond, "Betaine lipids in chlorarachniophytes," Phycological Research 58:298-305 (Oct. 2010; Wiley Online Library first published online: Sep. 28, 2010), Japanese Society of Phycology, Tokyo, Japan.

* cited by examiner

*Primary Examiner* — Patricia A Leith
*Assistant Examiner* — Erin M Bowers
(74) *Attorney, Agent, or Firm* — Sterne, Kessler, Goldstein & Fox P.L.L.C.

(57) ABSTRACT

To provide a method for supplying lauric acid with algae.
The method for producing an oil or fat containing lauric acid as a constituent fatty acid includes culturing algae in the class Chlorarachniophyceae in a medium and recovering, from the culture product, an oil or fat having a lauric acid content of 3 weight % or higher of the fatty acid composition.

2 Claims, No Drawings

METHOD OF PRODUCING LAURIC ACID OR AN ESTER THEREOF

FIELD OF THE INVENTION

The present invention relates to a method for producing an oil or fat containing lauric acid as a constituent fatty acid (hereinafter may also be referred to simply as "lauric acid-containing oil or fat"), the method employing algae.

BACKGROUND OF THE INVENTION

Lauric acid is a typical fatty acid contained in a large amount in coconut oil and palm kernel oil and is used as a raw material of a variety of surfactants, in foods, and for other materials.

Currently, the supply source of lauric acid is limited to coconut and palm kernels, which are grown in limited areas in the world. Cultivated lands now allocated to production of such lauric acid sources will be shared competitively with areas for bio-fuel for diesel engines and for food production. Excessive land cultivation for the production of lauric acid sources causes destruction of tropical rain forests.

Therefore, there is demand for creating a technique for supplying lauric acid, which technique does not rely on coconut or palm kernels.

Meanwhile, algae are known to effectively produce an oil or fat, and the productivity per area of the algae is about 10 times that of a plant or the like (Biotechnology Advances, (2007) 25, 294-306). Among algae, dinophyceae *Cryptheco-dinium chonii*, which grows not via photosynthesis but via heterotrophy, is known to be a lauric acid-producing organism and to have high lauric acid content (15.7%/total lipid) (Phytochemistry, (1988) 27, 1679-1683).

From the viewpoints of cost for carbon sources and other factors, more preferred are algae species which can grow via photosynthesis (autotrophy) and have higher lauric acid content. However, among such photoautotrophic algae species, only *Neochloris oleoabundans*, having a lauric acid content of about 1 to 2% at best, is known (J. Ind. Microbiol. Biotechnol. (2009) 36: 821-826), and no algae species has heretofore been known to have higher lauric acid content.

SUMMARY OF THE INVENTION

The present invention relates to a method for producing an oil or fat containing lauric acid as a constituent fatty acid, which method including culturing algae in the class Chlorarachniophyceae in a medium and recovering, from the culture product, an oil or fat having a lauric acid content of 3 weight % or higher of the fatty acid composition.

The present invention also relates to a method for producing lauric acid, which method including separating and recovering lauric acid from the oil or fat.

MODES FOR CARRYING OUT THE INVENTION

The present invention provides a method for supplying lauric acid through employment of algae.

The present inventors have carried out studies on lauric acid-producing organisms, and have found that the algae in the class Chlorarachniophyceae, which are a photoautotrophic unicellular algae, have high lauric acid content, and that an oil or fat containing lauric acid as a constituent fatty acid at high content can be efficiently produced by use of the algae.

According to the method of the present invention, which employs algae that can readily grow, an oil or fat containing lauric acid as a constituent fatty acid at high content can be efficiently produced, without imposing limitation on the cultivated fields for the growth of coconut and palm kernels or competing in the cultivated land with areas for food production, etc. In addition, according to the method of the present invention, destruction of tropical rain forests can be avoided.

The method of the present invention for producing a lauric acid-containing oil or fat includes culturing algae in the class Chlorarachniophyceae in a medium and recovering, from the culture product, an oil or fat having a lauric acid content of 3 weight % or higher in the fatty acid composition.

The oil or fat has a lauric acid content of 3 weight % or higher of the fatty acid composition. The lauric acid content is preferably 5 to 60 weight %, more preferably 10 to 60 weight %.

The algae employed in the present invention may be any algae strains in the class Chlorarachniophyceae, so long as the strains have an ability to produce an oil or fat having a lauric acid content of 3 weight % or higher in the fatty acid composition.

The algae of the present invention may be selected through, for example, the following screening procedure:

i) dispensing a sterilized medium (WA medium (see Table 2) as a fresh water medium or Daigo IMK medium (see Table 3) as a seawater medium) into a culture container;

ii) inoculating an alga strain to the medium and performing stationary culturing at room temperature (22° C. to 24° C.) under illumination (illuminance: about 3,000 lux, illumination for 12 hours and dark for 12 hours);

iii) recovering the produced alga and extracting oil or fat; methyl esterifying the fatty acids; and determining the fatty acid composition, to thereby select an alga strain which can produce a lauric acid-containing oil or fat; and iv) selecting an alga strain having a lauric acid content of 3 weight % or higher based on the total fatty acid in the oil or fat.

Examples of algae belonging to the class Chlorarachnion include algae belonging to the genus *Chlorarachnion*, *Lotharella*, *Gymnochlora*, *Cryptochlora*, and *Bigelowiella*. Among them, the genus *Lotharella*, *Gymnochlora*, and *Bigelowiella* are preferred.

Examples of more preferred algae belonging to the genus *Lotharella* include *Lotharella globosa*, *Lotharella amoebo-formis*, and *Lotharella vacuolata*. Examples of more preferred algae belonging to the genus *Gymnochlora* include *Gymnochlora stellata*. Examples of more preferred algae belonging to the genus *Bigelowiella* include *Bigelowiella natans*. Among *Lotharella globosa* strains, *Lotharella globosa* strain CCMP1729 is more preferred. Among *Lotharella amoebiformis* strains, *Lotharella amoebiformis* strain CCMP2058 is more preferred. Among *Lotharella vacuolata* strains, *Lotharella vacuolata* strain CCMP240 is preferred. Among *Gymnochlora stellata* strains, *Gymnochlora stellata* strain CCMP2057 is more preferred. Among *Bigelowiella natans* strains, *Bigelowiella natans* strains CCMP621 and CCMP2757 are more preferred (these strains are available from, for example, the Provasoli-Guillard National Center for Culture of Marine Phytoplankton (CCMP)). Strains having virtually the same phycological properties as those of algae strains are also more preferred. For example, in recent years, *Lotharella amoebiformis* has been proposed to be assigned to the new genus *Amorphochlora amoebiformis*. These strains are considered to have virtually the same phycological properties as those of *Lotharella amoebiformis*.

Examples of the strain having virtually the same phycological properties as those of *Lotharella amoebiformis* strain CCMP2058 include *Lotharella amoebiformis* strain Ryukyu. Examples of the strain having virtually the same phycological properties as those of *Lotharella vacuolata* strain CCMP240 include *Lotharella vacuolata* strain FK18G. Examples of the strain having virtually the same phycological properties as those of *Gymnochlora stellata* strain CCMP2057 include *Gymnochlora stellata* strain Guam-1. Examples of the strain having virtually the same phycological properties as those of *Bigelowiella natans* strains CCMP621 and CCMP2757 include *Bigelowiella natans* strains A11, 490, and VA3.

The aforementioned algae strains have the following phycological properties. Strains belonging to the same genus as that of the algae strains, and strains having virtually the same mycological properties as those of the algae strains can be identified on the basis of the following properties.

<Phycological Properties of the Algae in the Class Chlorarachniophyceae>
  i) Containing chlorophyll a and b
  ii) Chloroplast surrounded by four membranes
  iii) Having nucleomorph
  iv) Not accumulating starch
  v) Presence of amoeba phase and cell-wall-having phase
  vi) Having no stigma <Phycological Properties of the Algae Belonging to the Genus *Chlorarachnion*>
  i) Amoeboid vegetative cell
  ii) Nucleomorph in pyrenoid <Phycological Properties of the Algae Belonging to the Genus *Cryptochlora*>
  i) Spherical vegetative cell
  ii) Pyrenoid structure unknown <Phycological Properties of the Algae Belonging to the Genus *Lotharella*>
  i) The pyrenoid matrix was divided into two halves by a slit of the periplastidial compartment.
  ii) Nucleomorph present in the periphery of chloroplast in the vicinity of the pyrenoid base <Phycological Properties of the Algae Belonging to the Genus *Gymnochlora*>
  i) Inner membranes of chloroplast envelope invaginating pyrenoid matrix
  ii) Nucleomorph present in the periphery of chloroplast in the vicinity of the pyrenoid base <Phycological Properties of the Algae Belonging to the Genus *Bigelowiella*>
  i) Swarmers asexually proliferating
  ii) The pyrenoid matrix was slightly invaded by periplastidial compartment from the tip of the pyrenoid.
  iii) Nucleomorph present at the pyrenoid base <Phycological Properties of *Lotharella globosa* Strain CCMP1729>
  i) Spherical vegetative cell, no amoeba-like emerging upon proliferation <Phycological Properties of *Lotharella amoebiformis* Strain CCMP2058>
  i) Amoeba-like vegetative cell <Phycological Properties of *Lotharella vacuolata* Strain CCMP240>
  i) Spherical in the main stage of life cycle, amoeba-like cells having filopodia observed during the initial to middle culture stage
  ii) Having vacuoles larger than those of the other algae belonging to the genus *Lotharella*
  iii) Vegetative proliferation through binary fission of amoeba-like cells <Phycological properties of *Gymnochlora stellata* Strain CCMP2057>
  i) Star-shape amoebic organism having many filopodia not forming network
  ii) Cells having cell wall or swarmers are absent throughout the life cycle <Phycological Properties of *Bigelowiella natans* Strains CCMP621 and CCMP2757>
  i) Swarmers in the vegetative stage, not amoeba-like cells
  ii) Having two flagella (short and long)
  iii) Having no striae The algae of the present invention also encompass mutants of the aforementioned algae strains and strains having virtually the same mycological properties as those of the aforementioned algae strains.

For example, a mutant strain designed so as to produce an oil or fat having a higher lauric acid content as compared with a corresponding wild-type strain is also included in the algae of the present invention.

Furthermore, a gene derived from the algae in the class Chlorarachniophyceae of the present invention may be employed to produce an oil or fat having a high lauric acid content.

The algae in the class Chlorarachniophyceae of the present invention may be cultured in an appropriate medium prepared from natural or artificial seawater under illumination through a cultivation method generally employed in culturing of micro-algae.

The medium which may be employed in the invention is a known medium which contains natural or artificial seawater as a base, and additives such as a nitrogen source, a phosphorus source, a metal salt, and vitamins.

Examples of the nitrogen source include $NaNO_3$, $KNO_3$, $Ca(NO_3)_2$, $NH_4NO_3$, and $(NH_4)_2SO_4$. Examples of the phosphorus source include $K_2HPO_4$, $KH_2PO_4$, $Na_2HPO_4$, $NaH_2PO_4$, and sodium glycerophosphate. Examples of the metal salt include $NaCl$, $KCl$, $CaCl_2$, $MgCl_2$, $Na_2SO_4$, $K_2SO_4$, $MgSO_4$, $Na_2CO_3$, $NaHCO_3$, $Na_2SiO_3$, $H_3BO_3$, $MnCl_2$, $MnSO_4$, $FeCl_3$, $FeSO_4$, $CoCl_2$, $ZnSO_4$, $CuSO_4$, and $Na_2MoO_4$. Examples of the vitamins include biotin, vitamin B12, thiamine-HCl, nicotinic acid, inositol, folic acid, and thymine.

The aforementioned medium may further contain an appropriate additive such as a carbon source or a trace metal, in order to promote production of lauric acid-containing oil or fat.

Examples of preferred media include Daigo IMK medium, f/2 medium, ESM medium, L1 medium, and MNK medium.

Preferably, the pH of the thus-prepared medium is adjusted to fall within a range of 7.0 to 8.0 through addition of an appropriate acid or base, and is sterilized in an autoclave before use.

In culturing, no particular limitation is imposed on the amount of algae inoculated to the culture medium. However, the amount is preferably 1.0 to 10.0% (vol/vol), more preferably 1.0 to 5.0% (vol/vol), with respect to the amount of culturing medium.

No particular limitation is imposed on the culture temperature, so long as the growth of the algae of the present invention is not adversely affected. Generally, the culturing is preferably performed at 10 to 30° C., more preferably 15 to 25° C.

Light irradiation may be performed under any conditions, so long as photosynthesis can be performed. Needless to say, either artificial light or sunlight may be employed.

The illuminance preferably falls within a range of 100 to 50,000 lux, more preferably 300 to 10,000 lux.

The pH during culturing is generally 6.5 to 8.5, preferably 7.0 to 8.0.

Culturing is performed so that an alga is grown in a high density. For example, the culturing period is 7 to 120 days, preferably 7 to 30 days. Any of aeration and agitation culturing, shake culturing, and stationary culturing may be employed.

After completion of culturing, an alga is separated through a customary method such as centrifugation or filtration. The thus-separated alga mass as is, or a broken product thereof obtained through sonication, by means of Dyno Mill or by other means is subjected to solvent extraction with organic solvent such as chloroform, hexane, butanol, methanol, or ethyl acetate, whereby lauric-acid-containing oil or fat can be recovered.

When a *Gymnochlora stellata* strain CCMP2057 is used, 100 g of the dry alga contain a lauric acid-containing oil or fat in an amount of about 5 to about 10 g. That is, the amount of lauric acid-containing oil or fat produced in 1 L of medium reaches about 0.02 to about 0.05 g.

In this case, the oil or fat has a lauric acid content as high as 4.0 to 8.5 weight % of the fatty acid composition. Thus, the amount of produced lauric acid in 1 L of medium is as high as about 0.0008 to about 0.0043 g.

Lauric acid may be separated from the lauric acid-containing oil or fat by transforming the oil or fat into a fatty acid mixture or an ester of a fatty acid through a known method; and recovering high concentration of lauric acid through the urea addition method, cooling separation, HPLC, supercritical liquid chromatography, etc.

EXAMPLES

Example 1

Culturing of Algae and Analysis of Fatty Acid Composition

From "The Provasoli-Guillard National Center for Culture of Marine Phytoplankton (CCMP)," the following 6 algae strains were obtained and employed in the experiments.

TABLE 1

Algae strains

| No. | genus/species |
|---|---|
| 1729 | *Lotharella globosa* |
| 2058 | *Lotharella amoebiformis* |
| 240 | *Lotharella vacuolata* |
| 2057 | *Gymnochlora stellata* |
| 621 | *Bigelowiella natans* |
| 2757 | *Bigelowiella natans* |

Culturing of algae was performed in the following methods. A commercial medium (Daigo IMK medium, product of Nihon Pharmaceutical Co., Ltd.) (composition, see Table 2) was employed as a seawater medium.

TABLE 2

Composition of IMK medium

| | for 1 L |
|---|---|
| $NaNO_3$ | 200 mg |
| $Na_2HPO_4$ | 1.4 mg |
| $K_2HPO_4$ | 5 mg |
| $NH_4Cl$ | 2.68 mg |
| Fe-EDTA | 5.2 mg |
| Mn-EDTA | 332 µg |
| $Na_2$-EDTA | 37.2 mg |
| $ZnSO_4 \cdot 7H_2O$ | 23 µg |
| $CoSO_4 \cdot 7H_2O$ | 14 µg |
| $Na_2MoO_4 \cdot 2H_2O$ | 7.3 µg |
| $CuSO_4 \cdot 5H_2O$ | 2.5 µg |
| $H_2SeO_3$ | 1.7 µg |
| $MnCl_2 \cdot 4H_2O$ | 180 µg |
| Thiamin • HCl | 200 µg |
| Biotin | 1.5 µg |
| Vitamin B12 | 1.5 µg |
| Artificial sea water | 35.96 g |

Sterilized culture tubes (16 mm×150 mm) (product of VWR) each plugged with a sponge stopper (60882-167, product of VWR) were used, and a sterilized medium (10 mL/tube) was dispensed to the tubes. Each alga strain (100 µL (in the case of liquid medium) or 1 platinum loop (in the case of solid medium)) was inoculated to a new culture medium. Stationary culturing was performed at room temperature (22° C. to 24° C.) under a fluorescent lamp (illuminance: about 3,000 lux, illumination for 12 hours and dark for 12 hours).

Through centrifugation of the alga culture at 3,000 rpm for 30 minutes, an alga pellet was obtained. The alga pellet was dried at 80° C. for about 3 hours to about 16 hours, to thereby obtain dry alga, and the weight of the dry product was measured. The dry product was suspended in 1% saline (0.5 mL), and 5 mg/mL 7-pentadecanone (10 µL) was added as an internal standard to the suspension. Subsequently, chloroform (0.5 mL) and methanol (1 mL) were added to the suspension, and the mixture was vigorously stirred and then allowed to stand for 30 minutes. Thereafter, chloroform (0.5 mL) and 1.5% KCl (0.5 mL) were added to the mixture and stirred, followed by centrifugation at 3,000 rpm for 15 minutes. The formed chloroform layer (lower layer) was recovered by using a Pasteur pipette.

The thus-prepared lipid fraction (about 500 µL) was treated with nitrogen to dryness, and 0.5 N potassium hydroxide/methanol solution (700 µL) was added to the dried fraction, and then incubated at 80° C. for 30 minutes. Subsequently, 14% boron trifluoride solution (product of SIGMA) (1 mL) was added to the fraction, and then incubated at 80° C. for 20 minutes. Then, hexane (1 mL) and saturated saline (1 mL) were added to the above mixture, and the mixture was allowed to stand at room temperature for 30 minutes. The thus-obtained hexane layer (upper layer) was recovered and analyzed by GC.

The GC analysis was performed under the following conditions: chromatograph, HP 7890A GC-FID (product of Agilent); column, DB-1 ms 30 m×200 µm×0.25 µm (product of J&W scientific); mobile phase, high-purity helium; flow rate, 1 mL/min; and temperature elevation, 100° C. (1 minute), 5° C./min, and 280° C. (20 minutes). As saturated fatty acid controls, the following commercial products (all produced from SIGMA) were purchased and analyzed: methyl laurate (C12), methyl myristate (C14), methyl palmitate (C16), and methyl stearate (C18). As unsaturated fatty acid controls, the following commercial products (all produced from SIGMA) were purchased and analyzed: methyl palmitoleate (C16:1), methyl oleate (C18:1), methyl linoleate (C18:2), methyl linolenate (C18:3), methyl eicosapentaenoate (C20:5), and methyl docosahexaenoate (C22:6). Identification of fatty acids was performed on the basis of coincidence in retention time between the fatty acid analyte and the corresponding standard. Lauric acid was also identified by GC-MS. C16 multi-unsaturated fatty acids were estimated from the GC-MS analytical results and are represented by C16:x (x is 2 or 3, wherein x represents the number of unsaturated bonds in fatty acid). The GC-MS analysis was performed under the following conditions: chromatograph, HP 7890A GC and 5975C MS (products of Agilent); column, DB-1 ms 30 m×200 μm×0.25 μm (product of J&W scientific); mobile phase, high-purity helium; flow rate, 1 mL/min; and temperature elevation, 100° C. (1 minute), 5° C./min, and 280° C. (20 minutes). The amount of a fatty acid ester detected through GC analysis was calculated with reference to the internal standard, and the sum of the amounts of fatty acids was employed as the total fatty acid amount. The value obtained by dividing the total fatty acid amount by the amount of dry alga and multiplying the ratio by 100 was employed as a fatty acid content (%).

Table 3 shows the fatty acid compositional data of tested algae species.

was inoculated into IMK medium (100 mL) at 2% (v/v) placed in a 200-mL Erlenmeyer flask, and stationary culturing was performed at room temperature (22° C. to 24° C.) under illumination (illuminance: about 3,000 lux, illumination for 12 hours and dark for 12 hours) for 31 days. The culture liquid was centrifuged at 3,000 rpm for 30 minutes, to thereby recover cells, which were then washed once with 1% (w/v) aqueous sodium chloride solution.

The alga which had been recovered from the culture liquid (100 mL) was dried at 80° C. for about 16 hours, and chloroform (2 mL) and methanol (4 mL) were added to the dried alga. The mixture was vigorously stirred and then allowed to stand for 30 minutes. Thereafter, chloroform (2 mL) and 1.5% KCl (2 mL) were added thereto, and the obtained mixture was stirred. The stirred mixture was centrifuged at 3,000 rpm for 15 minutes, and the chloroform layer (lower layer) was collected by using a Pasteur pipette. An aliquot (100 μL) was recovered from the collected chloroform layer and dried to solid through nitrogen gas sprayed thereto. The dried product was dissolved in chloroform (10 μL). An aliquot (1 μL) was sampled from the chloroform solution, and the neutral fat content thereof was determined by means of Iatroscan (product of Mitsubishi Kagaku Iatron, Inc.). As a result, neutral lipid (1.2 mg) was obtained from the culture liquid (100 mL).

TABLE 3

Fatty acid composition analysis

| | Age | Fatty acid composition (%) | | | | | | | | | Productivity |
|---|---|---|---|---|---|---|---|---|---|---|---|
| No. | (days) | C12:0 | C14:0 | C16:0 | C18:0 | C18:1 | C18:2 | C18:3 | C20:5 | C22:6 | (mg/L) |
| 1729 | 28 | 13.0 | 1.9 | 25.5 | 1.8 | 0.0 | 4.0 | 2.0 | 38.2 | 13.5 | 10.0 |
| 2058 | 56 | 9.3 | 3.2 | 40.5 | 2.0 | 0.0 | 1.7 | 0.0 | 30.1 | 13.3 | 7.0 |
| 240 | 56 | 3.3 | 0.0 | 42.1 | 2.3 | 0.0 | 9.1 | 0.0 | 24.7 | 18.4 | 4.1 |
| 2057 | 40 | 8.5 | 5.1 | 50.6 | 6.6 | 3.6 | 5.2 | 0.0 | 0.0 | 20.4 | 35.9 |
| 621 | 33 | 5.9 | 8.4 | 34.1 | 2.9 | 7.4 | 0.0 | 0.0 | 32.3 | 8.9 | 4.4 |
| 2757 | 33 | 4.2 | 8.1 | 43.5 | 4.7 | 9.0 | 0.0 | 0.0 | 22.6 | 7.9 | 3.8 |

Accumulation of lauric acid (≧3% of the total fatty acids) was observed in *Lotharella globosa* strain CCMP1729, *Lotharella amoebiformis* strain CCMP2058, *Lotharella vacuolata* strain CCMP240, *Gymnochlora stellata* strain CCMP2057, and *Bigelowiella natans* strains CCMP621 and CCMP2757. Particularly, in *Gymnochlora stellata* strain CCMP2057, high fatty acid productivity and high-level accumulation of lauric acid (about 8.5% of the total fatty acids) were observed.

Example 2

Production of Alga Oil Having High Lauric Acid Content

An oil or fat having high lauric acid content was produced in the following manner.

*Gymnochlora stellata* CCMP2057 was subjected to stationary culturing in culture tubes (16 mm×150 mm, containing IMK medium (10 mL)) at room temperature (22° C. to 24° C.) under illumination (illuminance: about 3,000 lux, illumination for 12 hours and dark for 12 hours) for four weeks, to thereby produce a seed culture liquid. The seed culture liquid Through a methyl esterification method similar to that described in Example 1, an aliquot (500 μL) of the above-collected chloroform layer was analyzed. As a result, the total amount of the fatty acids obtained from the culture liquid (100 mL) was 6.2 mg, and the lauric acid content of the total fatty acid was 4.9%. That is, lauric acid (0.3 mg) was recovered from the culture liquid (100 mL).

The invention claimed is:

1. A method for producing lauric acid or an ester thereof, which method comprising
   (a) culturing *Chlorarachniophyceae* algae strain CCMP 1729 in a medium,
   (b) recovering the algae produced by said culturing,
   (c) recovering, from said algae produced by said culturing, an oil or fat having a lauric acid content of 3 weight % or higher of said oil's or fat's fatty acid composition,
   (d) separating the lauric acid from the oil or fat, and
   (e) recovering the lauric acid that has been separated from said oil or fat.

2. The method according to claim 1, wherein culturing is performed for 7 to 120 days under light irradiation at an illuminance of 300 to 10,000 lux.

* * * * *